United States Patent [19]

Perregaard et al.

[11] Patent Number: 5,428,036
[45] Date of Patent: Jun. 27, 1995

[54] SERTINDOLE PRODRUGS, COMPOSITIONS AND USE

[75] Inventors: Jens K. Perregaard, Jaegerspris; Henrik Pederson, Broenshoej, both of Denmark

[73] Assignee: H. Lundbeck A/S, Copenhagen-Valby, Denmark

[21] Appl. No.: 39,228

[22] Filed: Mar. 30, 1993

[30] Foreign Application Priority Data

Oct. 3, 1990 [DK] Denmark ............... 2381/90

[51] Int. Cl.$^6$ ............ A61K 31/445; A61K 31/535; C07D 401/14; C07D 413/14
[52] U.S. Cl. ............ 514/235.2; 514/323; 544/130; 546/201
[58] Field of Search ............ 544/130; 546/201; 514/235.2, 323

[56] References Cited

U.S. PATENT DOCUMENTS

| | | |
|---|---|---|
| 3,408,356 | 10/1968 | Horovitz . |
| 3,996,211 | 12/1976 | Lassen . |
| 4,038,305 | 7/1977 | Eliasson et al. . |
| 4,710,500 | 12/1987 | Perregaard . |

FOREIGN PATENT DOCUMENTS

| | | |
|---|---|---|
| 0167449 | 1/1986 | European Pat. Off. . |
| 0260070 | 9/1987 | European Pat. Off. . |
| 0392959 | 3/1990 | European Pat. Off. . |
| 2054371 | 6/1980 | United Kingdom . |
| 91/00168 | 6/1991 | WIPO . |

OTHER PUBLICATIONS

H. Bundgaard, "Design of Prodrugs", Elsevier (1985), Chapter 4, pp. 157–176.
J. Hyttel et al. *Pharmacology and Toxicology*, 61:126–129, 1987.

*Primary Examiner*—Robert W. Ramsuer
*Attorney, Agent, or Firm*—Darby & Darby

[57] ABSTRACT

Reaction products of sertindole with an acid or an activated acid, with formaldehyde alone, formaldehyde in the presence of an alcohol or an amine, or with an acyloxymethylene halide, and having general formula (1) wherein X is CO, CS, or $CH_2$, and if X is CO or CS, R is (i) hydrogen, alkyl, alkenyl, cycloalkyl, cycloalkenyl or cycloalk(en)ylalk(en)yl optionally substituted with hydroxy, or optionally substituted phenyl; or (ii) $YR^1$, wherein Y is O or S and $R^1$ is one of the substituents defined for R under (i) above; or (iii) $NR^2R^3$, wherein $R^2$ and $R^3$ independently are selected from the substituents defined for R under (i) above or $R^2$ and $R^3$ are combined to form a heterocyclic ring; or if X is $CH_2$, R is: (iv) a group $YR^1$ as defined in (ii); (v) a group $NR^2R^3$ as defined in (iii); or (vi) a group $OC(O)R^4$, wherein $R^4$ is as defined for $R^1$; are prodrugs of sertindole and show sustained release of sertindole when injected as formulated in a suitable oil. The compounds are useful in the treatment of mental disorders such as schizophrenia including both negative and positive symptoms, non-schizophrenic psychoses, depression and anxiety.

11 Claims, 2 Drawing Sheets

SERTINDOLE PRODRUGS, COMPOSITIONS AND USE

This application is a continuation of PCT/DK91/0029, filed Sep. 27, 1991. The present invention relates to novel derivatives of the atypical neuroleptic compound sertindole (recommended INN name), 5-chloro-1-(4-fluorophenyl)-3-[1-[2-(2-imidazolidinon-1-yl)ethyl]-4-piperidyl]-1H-indole, which derivatives are reaction products from the reaction of sertindole with an acid or an activated acid derivative, from the reaction of sertindole with acyloxymethylene halides, or from the reaction of sertindole with formaldehyde alone or in the presence of an alcohol or an amine. Such reaction products are useful in the treatment of mental disorders such as schizophrenia including both negative and positive symptoms, non-schizophrenic psychoses, depression and anxiety.

Sertindole is disclosed in U.S. Pat. No. 4,710,500, corresponding to EP 0200322 B1. The neuroleptic action of sertindole without causing the side effects of classical neuroleptics is described in our copending European patent application No. EP 0392959 A2, and the anxiolytic action is descibed in our copending International Patent Application No. PCT/DK91/00168.

It is well known that prodrugs and long-acting derivatives of drugs may be obtained by esterifying a present hydroxyl group. U.S. patent application Ser. No. 3,408,356 relates to long chain esters of certain (hydroxypiperidino)butyrophenones which are stated to be long acting tranquillizers. GB Patent Application No. 2,054,371 and European Patent Publication No 260,070 disclose the prolonged action of haloperidol decanoate and acetate, respectively, and U.S. Pat. Nos. 3,996,211 and 4,038,395 describe acyl derivatives of clopentixol. Furthermore, Anthony A. Sinkula (1985) "Sustained Drug Action Accomplished by the Prodrug Approach" in Design of Prodrugs (Hans Bundgaard ed.), Elsevier Science Publishers B.V., describes a number of prodrugs, such as steroid esters, prodrug esters of neuroleptics, bambuterol (bis-N,N-dimethylcarbamate prodrug of terbutaline) and polymeric prodrugs.

Classical neuroleptics are known to cause extrapyramidal side effects (e.g. dystonia, akathisia and parkinsonism) and accordingly give concern among clinicians. In view of the long period of application of neuroleptics, the nature of the disease and the well recognized advantages of using depot preparations in the treatment thereof, there is a great demand for long acting neuroleptics whithout the side effects of classical neuroleptics.

It has now surprisingly been found that reaction products of sertindole with an acid or an activated acid derivative, with formaldehyde alone or formaldehyde in the presence of an alcohol or an amine, or with an acyloxymethylene halide, are prodrugs of sertindole, which decompose into sertindole over a desired period of time when formulated in a proper pharmaceutical form.

Accordingly the present invention relates to novel prodrugs of sertindole which are reaction products of sertindole with an acid or an activated acid, with formaldehyde alone, with formaldehyde in the presence of an alcohol or an amine, or with an acyloxymethylene halide;, and have the general formula 1:

wherein X is selected from CO, CS, or $CH_2$, and if X is CO or CS, R is selected from the groups consisting of:
   i) hydrogen, alkyl, alkenyl, cycloalkyl, cycloalkenyl or cycloalk(en)ylalk(en)yl, optionally substituted with one or two hydroxy groups, or phenyl optionally substituted with one or more substituents selected from the group consisting of halogen, trifluoromethyl, lower alkyl, lower alkoxy, lower alkylthio, acyloxy, or cyano; or
   ii) $YR^1$, wherein Y is O or S and $R^1$ is selected from the substituents defined for R under i) above; and
   iii) $NR^2R^3$, wherein $R^2$ and $R^3$ independently are selected from the substituents defined for R under i) above, or $R^2$ and $R^3$ are combined to form a four to eight membered heterocyclic ring containing from one to three nitrogen atoms and from zero to three oxygen or sulfur atoms; or if X is $CH_2$, R is selected from the groups consisting of:
   iv) a group $YR^1$ as defined in ii);
   v) a group $NR^2R^3$ as defined in iii); or
   vi) a group $OC(O)R^4$, wherein $R^4$ is as defined for $R^1$;

and pharmaceutically acceptable salts thereof.

Any isomer, such as optically active isomers and regioisomers of the compounds of formula 1 are embraced by the invention.

So, a compound of the invention may possibly be obtained as a regioisomer having the following structure 2 wherin $R^1$ and X are as defined in Structure 1, or as a mixture of the two isomers of formulas 1 and 2. Generally O-acylated derivatives 2 are more labile and expected to rearrange to the corresponding N-acyl derivatives 1. Similar rearrangement reactions are generally known in the literature (Kohn et al., *J. Org. Chem.* 1977, 42 (6), 941–948 and *Organic Reactions* 1965 14,1 ) as the (Chapman rearrangement.

The term "alkyl" is intended to mean a straight chain or branched alkyl group having from one to twentyfour carbon atoms, inclusive. The term "alkenyl" is similarly intended to mean a straight chain or branched alkenyl group having from two to twentyfour carbon atoms, inclusive. The terms "cycloalkyl" and "cycloalkenyl" comprise saturated and unsaturated carbocyclic rings, respectively, containing from three to eight carbon atoms, inclusive.

The term "lower alkyl" is intended to mean a straight chain or branched alkyl group having from one to four carbon atoms, such as methyl, ethyl, n-propyl, iso-propyl, n-butyl, sec-butyl, etc. Lower alkoxy, and lower alkylthio similarly designate such groups wherein the alkyl moiety is a lower alkyl group as defined above.

Lower alkenyl is intended to mean an alkenyl group containing from two to four carbon atoms, for example ethenyl, 1-propenyl, 2-butenyl, etc.

Preferred compounds of the invention are those of structure 1 wherein
a) X is CO and R is $C_1$-$C_{10}$-alkyl or optionally substituted phenyl; or
b) X is $CH_2$ and R is a group $NR^2R^3$, $R^2$ being hydrogen or $C_1$-$C_{10}$-alkyl and $R^3$ being $C_1$-$C_{10}$-alkyl; a 1-morpholino group; a group $OCOR^4$, $R^4$ being $C_1$-$C_{10}$-alkyl; or a group $YR^1$ wherein Y is O and $R^1$ is $C_1$-$C_{10}$-alkyl.

Particularly preferred compounds of the present invention are:
3-[1-[2-(3-Acetyl-2-imidazolidinon-1-yl)ethyl]-4-piperidyl]-5-chloro-1-(4-fluorophenyl)-(1H-indole,
5-chloro-3-[1-[2-(3-decanoyl-2-imidazolidinon-1-yl)ethyl]-4-piperidyl]-1-(4-fluorophenyl)-1H-indole,
3-[1-[2-(3-benzoyl-2-imidazolidinon-1-yl)ethyl]-4-piperidyl]-5-chloro-1-(4-fluorophenyl)-1H-indole,
5-chloro-1-(4-fluorophenyl)-3-[1-[2-[3-(1-morpholinomethyl)-2-imidazolidinon-1-yl]-ethyl]-4-piperidyl]-1H-indole,
5-chloro-1-(4-fluorophenyl)-3-[1-[2-(3-butanoyl-2-imidazolidinon-1-yl)ethyl]-4-piperidyl]-1H-indole,
5-chloro-3-[1-[2-[3-(1-decanyl)oxymethyl-2-imidazolidinon-1-yl]ethyl]-4-piperidyl]-1-(4-fluorophenyl)-1H-indole,
5-chloro-1-(4-fluorophenyl)-3-[1-[2-(3-hexanoyl-2-imidazolidinon-1-yl)ethyl]-4-piperidyl]-1H-indole, and
5-chloro-1-(4-fluorophenyl)-3-[1-[2-(3-octanoyl-2-imidazolidinon-1-yl)ethyl]-4-piperidyl]-1H-indole.

Other specific compounds within the scope of the present invention include the following:
5-Chloro-1-(4-fluorophenyl)-3-[1-[2-(3-pivaloyl-2-imidazolidinon-1-yl)ethyl]-4-piperidyl]-1H-indole,
5-chloro-3-[1-[2-(3-cyclohexylcarbonyl-2-imidazolidinon-1-yl)ethyl]-4-piperidyl]-1-(4fluorophenyl)-1H-indole,
5-chloro-1-(4-fluorophenyl)-3-[1-[2-(3-hexadecanoyl-2-imidazolidinon-1-yl)-ethyl]-4-piperidyl-1H-indole,
5-chloro-1-(4-fluorophenyl)-3-[1-[2-[3-(2,4,6-trimethylbenzoyl)-2-imidazolidinon-1-yl]ethyl]-4-piperidyl]-1H-indole,
5-Chloro-1-(4-fluorophenyl)-3-[1-[2-(3-oleyl-2-imidazolidinon-1-yl)ethyl]-4-piperidyl]-1H-indole,
5-chloro-1-(4-fluorophenyl)-3-[1-[2-[3-(1-nonyl)aminocarbonyl-2-imidazolidinon-1-yl]ethyl]-4-piperidyl]-1H-indole,
5-chloro-3-[1-[2-(3-dimethylcarbamyl-2-imidazolidinon-1-yl)ethyl]-4-piperidyl]-1-(4-fluorophenyl)-1H-indole,
5-chloro-3-[1-[2-(3-dimethylthiocarbamyl-2-imidazolidinon-1-yl)ethyl]-4-piperidyl]-1-(4-fluorophenyl)-1H-indole,
5-chloro-1-(4-fluorophenyl)-3-[1-[2-(3-methoxycarbonyl-2-imidazolidinon-1-yl)ethyl]-4-piperidyl]-1H-indole,
5-chloro-3-[1-[2-[3-(1-decyl)oxycarbonyl-2-imidazolidinon-1-yl]ethyl]-4-piperidyl]-1-(4-fluorophenyl)-1H-indole,
5-chloro-1-(4-fluorophenyl)-3-[1-[2-(3-hydroxymethyl-2-imidazolidinon-1-yl)ethyl]-(4-piperidyl]-1H-indole
5-chloro-3-[1-[2-(3-dimethylaminomethyl-2-imidazolidinon-1-yl)ethyl]-4-piperidyl]-1-(4-fluorophenyl)-1H-indole,
5-chloro-3-[1-[2-(3-dipropylaminomethyl-2-imidazolidinon-1-yl)ethyl]-4-piperidyl]-1-(4-fluorophenyl)-1H-indole,
5-chloro-3-[1-[2-(3-t-butylaminomethyl-2-imidazolidinon-1-yl)ethyl]-4-piperidyl]-1-(4-fluorophenyl)-1H-indole,
5-chloro-3-[1-[2-(3-ethoxymethyl-2-imidazolidinon-1-yl)ethyl]-4-piperidyl]-1-(4-fluorophenyl)-1H-indole,
5-chloro-1-(4-fluorophenyl)-3-[1-[2-(3-methoxymethyl-2-imidazolidinon-1-yl)ethyl]-4-1H-indole,
5-chloro-1-(4-fluorophenyl)-3-[1-[2-[3-(2-propyl)oxymethyl-2-imidazolidinon-1-yl]ethyl]-4-piperidyl]-1H-indole,
5-chloro-1-(4-fluorophenyl)-3-[1-[2-[3-(4-isopropylbenzoyl)-2-imidazolidinon-1-yl]ethyl]-4-piperidyl]-1H-indole,
5-chloro-3-[1-[2-[3-(2-chlorobenzoyl)-2-imidazolidinon-1-yl]ethyl]-4-piperidyl]-1-(4-fluorophenyl)-1H-indole,
3-[1-[2-[3-(2-acetyloxybenzoyl)-2-imidazolidinon-1-yl]ethyl]-4-piperidyl]-5-chloro-1-(4-fluorophenyl)-1H-indole,
5-chloro-1-(4-fluorophenyl)-3-[1-[2-(3-pivaloyloxymethyl-2-imidazolidinon-1-yl)ethyl]-4-piperidyl]-1H-indole.

The compounds are soluble in pharmaceutically acceptable oils under sterile conditions. When administered intra muscularis in an appropriate pharmaceutically acceptable oil, release from the oil and decomposition of the compounds of the invention into sertindole takes place in such a way that sertindole is released to the body over a desirable prolonged period of time.

The reaction products of the present invention may be divided into acylated derivatives of sertindole and derivatives which are reaction products with an acyloxymethylene halide or with formaldehyde alone or formaldehyde combined with an alcohol or amine.

Known depot derivatives of neuroleptics are carboxylic acid esters of neuroleptics comprising a free hydroxy group. Contrary to said known acylated derivatives, the acylated reaction products of sertindole are not esters but acylated imidazolidin-2-on derivatives. Therefore, the fact that they can exist (are stable in a suitable pharmaceutical formulation) and decompose properly is indeed surprising. This is stressed by the fact that they are not decomposed to sertindole in an in vitro test comprising incubation with rat or pig liver homogenate or human plasma, in which test prodrugs are expected to decompose, whereas they decompose properly in vivo.

With respect to the other derivatives of the present invention, the concept of using such types of reactants in the formation of prodrugs is new and, accordingly, it is surprising that such derivatives decompose properly to the mother sertindole.

Consequently, the compounds of the present invention are very promising drugs which, when formulated in appropriate pharmaceutical compositions, are useful as depot drugs for the treatment of mental disorders such as schizophrenia including both negative and positive symptoms, non-schizophrenic psychoses, depression and anxiety and any other indication in which sertindole might be useful and for which depot formulations are advantageous.

Accordingly, in a second aspect the present invention relates to a depot formulation of sertindole comprising a prodrug of the invention in a suitable pharmaceutical formulation, in particular a depot formulation of sertindole comprising a prodrug of the invention in a properly selected pharmaceutically acceptable oil.

The preferred oils are of vegetable origin such as coconut oil, e.g. viscoleo®, peanut oil, sesame oil, cotton seed oil, corn oil, soy bean oil, olive oil etc. or they are synthetic esters of fatty acids and polyfunctional alcohols, such as glycerol or propylenglycol.

An appropriate dose of a compound in accordance with the invention is from about 0.01 to 10 mg/kg body weight per injection. Preferably, the preparations of the invention are presented as unit dose preparations comprising about 0.5 to 5.0 ml of a 0.1 to 20% weight/weight solution calculated as the weight of sertindole corresponding to the amount of compound of the invention present in the oil.

The compositions of the present invention are prepared by dissolving a compound of the invention in a pharmaceutically acceptable oil under sterile conditions. The oil is selected so as to obtain a release of the active ingredient over a desired period of time. The proper oil may easily be determined by a person skilled in the art by due experimentation.

These novel preparations are useful as injectable depot formulations of sertindole, with a duration of action ranging from about one week to six months.

In a further aspect the invention provides a method for preparing the prodrugs of the invention comprising:

a) reacting sertindole alone or in the presence of a suitable base in an inert organic solvent with a carboxylic acid halide RCO-hal or a symmetrical or mixed carboxylic acid anhydride RCO—O—OCR′, wherein R is as defined previously under i) to iii) in formula 1, hal is chlorine or bromine, and R′CO—O— constitute a proper leaving group as e.g. $CH_3CH_2OCOO—$, $CH_3COO—$; or b) reacting sertindole alone or in the presence of a suitable base in an inert organic solvent with a carbonic or thiocarbonic acid halide of the following formula $R^1—Y—CY^1—hal$ or $R^2R^3N—CY^1—hal$, wherein $R^1$, $R^2$, $R^3$, and Y are as previously defined and $Y^1$ is oxygen or sulphur and hal is chlorine or bromine; or c) reacting sertindole in an inert organic solvent with an isocyanate or an isothiocyanate of the following formula $R^1—N=C=Y^1$, wherein $R^1$ is as previously defined and $Y^1$ is as defined above, or d) reacting sertindole with a carboxylic acid RCOOH, wherein R is as defined previously under i) to iii) in formula 1, in an inert organic solvent containing a coupling reagent, and optionally a basic catalyst; or e) reacting sertindole with one equivalent of formaldehyde in an inert organic solvent; or f) reacting sertindole with one equivalent of formaldehyde in the presence of an amine or an alcohol in an inert solvent or without a solvent. Acid catalysts are preferably added when alcohols participate in the reaction; or g) reacting sertindole in an inert organic solvent with an acyloxymethylene halide like hal—$CH_2$—O(-CO)$R^4$, wherein $R^4$ is as previously defined and hal is a leaving group like chlorine, bromine, or iodine.

In Method a) and b) a suitable base is e.g. potassium t-butoxide, sodium or potassium amide, sodium hydride, sodium or potassium hydroxide, or sodium or potassium carbonate. Preferred inert solvents are toluene, diethyl ether, tetrahydrofurane, N,N-dimethylformamide, N-methylpyrrolidone or dimethylsulfoxide. The reaction is preferably performed at temperatures from −20° C. to the boiling point of the solvent.

In Method c) a suitable inert organic solvent is for example dichloromethane, 1,1,1-trichloroethane, chloroform, tetrahydrofurane, or dioxane.

In Method d) an appropriate inert organic solvent is dichloromethane, 1,1,1-trichloroethane, chloroform, tetrahydrofurane, dioxane, toluene or dimethylformamide, an appropriate coupling reagent is a dialkylcarbodiimid, e.g. dicyclohexyl or diisopropyl, and the basic catalyst may be pyridine, triethylamine, 4-dimethylaminopyridine, 4-pyrrolidinopyridine or the like. Other possible coupling reagents are for example pentahalophenol complexes with dialkylcarbodiimides, substituted cyanamides, ketenimines and ketenes. When pyridin or triethylamin is used as basic catalyst, they may conveniently also constitute the solvent.

In Methods e) and f) preferred inert solvents are tetrahydrofuran, toluene, acetone or when alcohols are used these might conveniently constitute the solvent. Preferred reaction temperatures are from room temperature to slightly elevated temperatures such as 40°–60° C. Acid catalysts are e.g. acetic, trifluoroacetic, or mineral acids (HBr, HCl).

The reaction conditions in Method g) are as described above according to Methods a) and b).

The present invention is illustrated in the following by examples with reference to the drawings in which.

EXAMPLES

The examples are given only for the purpose of illustration and may in no way be construed as limiting for the invention.

Structural Assignment

Compounds prepared according to Methods e) and f) were unequivocally assigned as having Structure 1 by $^1$H NMR nuclear Overhauser enhancement effects. The acetylated compound, Example 1a below, was shown by X-ray analysis to be the N-acetylated derivative of Structure 1. All other acylated derivatives are also most likely N-acylated derivatives of Structure 1 according to their $^1$H NMR spectra. However, it is not impossible that in certain cases, the compounds may possibly exist as Structure 2, or a mixture of the two structures as well.

Preparation examples

¹H NMR spectra were recorded for the free bases from Examples 1-5 and 8 in chloroform-d at ambient temperature unless otherwise stated and for the salts from Examples 6-7 in dimethylsulfoxide-d₆ at ambient temperature unless otherwise stated at 250 MHz on a Bruker AC-250 instrument. TMS was added as internal reference standard. In the listing of NMR data the following abbreviations are used: d=doublet, dq=double quartet, dt=double triplet, h=heptet, m=multiplet, q=quartet, qui=quintet, s=singlet, sx=sextet, t=triplet, tt=triple triplet. In the case of addition salts, the signals from acidic hydrogens are omitted.

Example 1 (Method a)

3-[1-[2-(3-Acetyl-2-imidazolidinon-1-yl)ethyl]-4-piperidyl]-5-chloro-1-(4-fluorophenyl)-1H-indole, fumarate, 1a To a well-stirred suspension of potassium t-butoxide (1.2 g) in dry toluene (100 ml) kept at 0° C. was added 5-chloro-1-(4-fluorophenyl)-3-[1-[2-(2-imidazolidinon-1-yl)ethyl]-4-piperidyl]-1H-indole (4.4 g). The mixture was heated and stirred for 1.5 h at 50° C. To the thus prepared potassium salt was added dropwise at 0° C. a solution of acetyl chloride (0.8 g) in dry toluene (20 ml). The mixture was finally allowed to reach room temperature and was subsequently poured into ice. Ether (100 ml) and a 2M NH₄OH solution (10 ml) were added, the organic phase was separated, dried (anh. MgSO₄) and the solvent evaporated. Finally column chromatography on silica gel (eluted with ethyl acetate/methanol 2:1) yielded the title compound as a pure product. Yield 2.5 g MP: 127°-128° C. The fumaric acid salt crystallized from ethanol. MP: 168°-170° C. ¹H NMR: δ1.79 (2H, dq), 2.08 (2H, broad d), 2.22 (2H, t), 2.51 (3H, s), 2.60 (2H, t), 2.82 (1H, tt), 3.08 (2H, broad d), 3.45 (2H, t), 3.83 (2H, t), 7.0–7.7 (8H).

In a corresponding manner the following carboxylic acid derivatives were prepared:

5-chloro-3-[1-[2-(3-decanoyl-2-imidazolidinon-1-yl)ethyl]-4-piperidyl]-1-(4-fluorophenyl)-1H-indole, oxalate, 1b, MP:179°-181° C. ¹H NMR: δ0.85 (3H, t), 1.25 (12H, broad s), 1.61 (2H, qui), 1.76 (2H, dq), 2.06 (2H, broad d), 2.21 (2H, t), 2.60 (2H, t), 2.82 (2H, tt), 2.93 (2H, t), 3.07 (2H, broad d), 3.44 (2H, t), 3.85 (2H, t), 7.0–7.7 (8H);

5-chloro-1-(4-fluorophenyl)-3-[1-[2-(3-pivaloyl-2-imidazolidinon-1-yl)ethyl]-4-piperidyl]-1H-indole, oxalate, 1c, MP: 186° C. ¹NMR: δ1.40 (9H, s), 1.76 (2H, dq), 2.08 (2H, broad d), 2.21 (2H, t), 2.59 (2H, t), 2.81 (1H, tt), 3.08 (2H, broad d), 3.43 (2H, t), 3.49 (2H, t), 3.85 (2H, t), 7.0–7.7 (8H;

5-chloro-3-[1-[2-(3-cyclohexylcarbonyl-2-imidazolidinon-1-yl)ethyl]-4-piperidyl]-1-(4-fluorophenyl)-1H-indole, oxalate, 1d, MP: 189° C. ¹H NMR: δ1.13–1.60 (6H, m), 1.61–1.98 (6H, m), 2.08 (2H, broad d), 2.21 (2h, t), 2.62 (2H, t), 2.82 (1H, tt), 3.07 (2H, broad d), 3.44 (2H, t), 3.52 (2H, t), 3.62 (1H, m), 3.82 (2H, t), 7.0–7.7 (8H);

5-chloro-1-(4-fluorophenyl)-3-[1-[2-(3-hexadecanoyl-2-imidazolidinon-1-yl)ethyl]-4-piperidyl]-1H-indole, oxalate, 1e, MP: 159°-160° C. ¹H NMR: δ0.87 (3H, t), 1.23 (24H, broad s), 1.65 (2H, qui), 1.76 (2H, dq), 2.08 (2H, broad d), 2.23 (2H, t), 2.61 (2H, t), 2.82 (1H, tt), 2.93 (2H, t), 3.09 (2H, broad d), 3.47 (2H, t), 3.52 (2H, t), 3.84 (2H, t), 7.0–7.7 (8H);

3-[1-[2-(3-benzoyl-2-imidazolidinon-1-yl)ethyl]-4-piperidyl]-5-chloro-1-(4-fluorophenyl)-1H-indole, oxalate 1f, MP:231°-233° C. ¹H NMR: δ1.78 (2H, dq), 2.08 (2H, broad d), 2.19 (2H, t), 2.57 (2H, t); 2.82 (1H, tt), 3.05 (2H, broad d), 3.43 (2H, 3.62 (2H, t), 4.04 (2H, t), 7.0–7.7 (13H);

5-chloro-1-(4-fluorophenyl)-3-[1-[2-[3-(2,4,6-trimethylbenzoyl)-2-imidazolidinon -1-yl]ethyl]-4-piperidyl]-1H-indole, oxalate, 1 g, MP: 206°-207° C. ¹H NMR: δ1.73 (2H, dq), 2.05 (2H, broad d), 2.16 (2H, t), 2.18 (6H, s), 2.22 (3H, s), 2.66 (2H, t), 2.79 (1H, tt), 3.02 (2H, broad d), 3.49 (2H, t), 4.08 (2H, t), 6.80 (2H, s), 7.0–7.7 (8H).

Example 2 (Method d),

5-Chloro-1-(4-fluorophenyl)-3-[1-[2-(3-oleyl-2-imidazolidinon-1-yl)ethyl]-4-piperidyl]-1H-indole, Fumarate, 2a To a stirred solution of 5-chloro-1-(4-fluorophenyl)-3-[1-[2-(2-imidazolidinon-1-yl)ethyl]-4-piperidyl]-1H-indole (5 g)in dichloromethane (40 ml) was added 1,3-dicyclohexylcarbodiimide (2.65 g), 4-pyrrolidinopyridine (0.17 g) and oleic acid (90%, food grade, 3.32 g). After stirring overnight at room temperature the mixture was filtered, and the filtrate was evaporated. The residue was eluted on silica gel with ethyl acetate/ethanol/diethylamine 87:10:3 to yield 1.4 g of pure product. The fumaric acid salt crystallized from acetone. MP: 131°-133° C. ¹H NMR: δ0.87 (3H, t), 1.28 (20H, broad s), 1.63 (2H, qui), 1.78 (2H, dq), 2.00 (4H, broad q), 2.08 (2H, broad d), 2.20 (2H, t), 2.60 (2H, t), 2.83 (1H, tt), 2.93 (2H, t), 3.09 (2H, b 3.46 (2H, t), 3.52 (2H, t), 3.85 (2H, t), 5.32, (2H, t), 7.0–7.7 (8H).

Example 3 (Method c)

5-Chloro-1-(4-fluorophenyl)-3-[1-[2-[3-(1-nonyl)aminocarbonyl-2-imidazolidin-1-yl]ethyl]-4-piperidyl]-1H-indole, oxalate, 3a 1-Nonyl isocyanate (1.9 g) and 5-chloro-1-(4-fluorophenyl)-3-[1-[2-(2-imidazolidinon-1-yl)ethyl]-4-piperidyl]-1H-indole (4.4 g) were refluxed in dry 1,1,1-trichloroethane (70 ml) for 16 hours. The solvent was evaporated and the remaining crude product was purified by column chromatography on silica gel (eluted with ethyl acetate/methanol 1:1 ). The free base of the title compound was obtained as a viscous oil. The oxalate salt precipitated from acetone. Yield 2.9 g. MP: 176°-178° C. ¹H NMR: δ0.87 (3H, t), 1.25 (12H, s), 1.53 (2H, qui), 1.78 (2H, dq), 2.06 (2H, broad d), 2.21 (2H, t), 2.60 (2H, t), 2.84 (1H, tt), 3.08 (2H, broad d), 3.28 (2H, q), 3.42 (2H, t), 3.53 (2H, t), 3.88 (2H, t), 7.0–7.7 (8H), 8.12 (1 H, t).

Example 4 (Method b)

5-Chloro-3-[1-[2-(3-dimethylcarbamyl-2-imidazolidinon-1-yl)ethyl]-4-piperidyl]-1-(4-fluorophenyl)-¹H-indole, hydrochloride, 4a To a solution of 5-chloro-1-(4-fluorophenyl)-3-[1-[2-(2-imidazolidinon-1-yl)ethyl]-1H-indole (8.8 g) in dry toluene (300 ml) was added potassium t-butoxide (2.5 g) at 0° C. The suspension was heated at 60° C. for 2 hours. After cooling to room temperature dimethylcarbamyl chloride (2.5 g) was added and the mixture was finally heated at 80° C. for 4 hours. The reaction mixture was poured onto ice and was subsequently extracted with ethyl acetate (2×100 ml). The organic phase was separated, dried and the solvent evaporated. The pure title compound was obtained by column chromatography on silica gel (eluted with ethyl acetate/methanol 2:1) as a viscous oil. The hydrochloride salt crystallized from acetone containing 10% of ethanol. Yield 5.4 g. MP:222°–224° C. $^1$H NMR: δ1.76 (2H, dq), 2.07 (2H, broad d), 2.20 (2H, t), 2.59 (2H, t), 2.80 (1H, tt), 3.04 (6H, s), 3.08 (2H, broad 3.42 (2H, t), 3.50 (2H, t), 3.75 (2H, t), 7.0–7.7 (8H).

In a corresponding manner the following carbonic acid derivatives were prepared:

5-chloro-3-[1-[2-(3-dimethylthiocarbamyl-2-imidazolidinon-1-yl)ethyl]-4-piperidyl]-1-(4-fluorophenyl)-1H-indole, oxalate, 4b, MP :140°–142° C. $^1$H NMR recorded at 360° K. in DMSO-d$_6$: δ1.71 (2H, dq), 1.97 (2H, broad d), 2.20 (2H, t), 2.52 (2H, t), 2.82 (1H, tt), 3.02 (2H, broad d), 3.23 (6H, s), 3.31 (2H, t), 3.45 (2H, t), 3.83 (2H, t), (2H); 7.1–7.7 (8H);

5-chloro-1-(4-fluorophenyl)-3-[1-[2-(3-methoxycarbonyl-2-imidazolidinon-1-yl)ethyl]-4-piperidyl]-1H-indole, hydrochloride, 4c, MP: 194°–195° C. $^1$H NMR: δ1.78 (2H, dq), 2.07 (2H, broad d), 2.20 (2H, t), 2.58 (2H, t), 2.80 (1H, tt), 3.08 (2H, broa 3.40 (2H, t), 3.51 (2H, t) 3.85 (2H, t), 3.86 (3H, s), 7.0–7.7 (8H);

5-chloro-3-[1-[2-[3-(1-decyl)oxycarbonyl-2-imidazolidinon-1-yl]ethyl]-4-piperidyl]-1-(4-fluorophenyl)-1H-indole, oxalate, 4d, MP: 114°–116° C. $^1$H NMR: δ0.88 (3H, t), 1.22 (14H, broad s), 1.70 (2H, dq), 1.78 (2H, dq), 2.06 (2H, broad d), 2.20 (2H, t), 2.59 (2H, t), 2.81 (1H, tt), 3.08 (2H, broad d), 3.43 (2H, t), 3.52 (2H, t), 3.82 (2H, t), 7.0–7.7 (8H).

Example 5 (Method e)

5-Chloro-1-(4-fluorophenyl)-3-[1-[2-(3-hydroxymethyl-2-imidazolidinon-1-yl)ethyl]-4-piperidyl]-1H-indole 5a To a solution of 5-chloro-1-(4-fluorophenyl)-3-[1-[2-(2-imidazolidinon-1-yl)ethyl]-4-piperidyl]-1H-indole (4.4 g) in tetrahydrofuran (25 ml) at room temperature was added dropwise a 30% aqueous solution of formaldehyde (800 mg). The mixture was heated at 50° C. for 2 h. Solvents were evaporated in vacuo and excess H$_2$O was removed by evaporation with toluene. By addition of acetone the title compound crystallized. Recrystallization from acetone afforded 3.2 g of pure 5a. Mp: 118°–119° C. $^1$H NMR: δ1.85 (2H, dq), 2.05 (2H, broad d), 2.20 (2H, t), 2.60 (2H, t), 2.85 (1H, tt), 3.10 (2H, broad d), 3.40 (2H, t), 3.50 (4H, t), 4.80 (2H, s), 7.0–7.7 (8H).

Example 6 (Method f)

5-Chloro-1-(4-fluorophenyl)-3-[1-[2-[3-(1-morpholinomethyl)-2-imidazolidinon-1-yl]ethyl]-4-piperidyl]-1H-indole, ditartrate, 6a To a solution of 5-chloro-1-(4-fluorophenyl)-3-[1-[2-(2-imidazolidinon-1-yl)ethyl]-4-piperidyl]-1H-indole (4.4 g) in tetrahydrofuran (50 ml) were added morpholine(900 mg), and 30% aqueous formaldehyde (1.7 g) successively. The mixture was refluxed for 3 h and finally poured into ice (500 g). Ethyl acetate was added and pH was adjusted to >9 by addition of aqueous NH$_4$OH. The organic phase was separated and worked-up as above. The crude product was purified by column chromatography (eluted with ethyl acetate/tetrahydrofuran/triethylamine 60:40:4). The pure title compound thus isolated was crystallized as the ditartaric acid salt from acetone. Yield: 2.8 g. Mp: 180° C. (decomp.). $^1$H NMR: δ1.82 (2H, dq), 2.08 (2H, broad d), 2.43 (4H, t), 2.59 (2H, t), 2.84 (2H, t), 2.9 (1 H, tt), 3.31 (4H, m), 3.38 (4H, s), 3.55 (4H, t), 3.79 (2H, s), 4.20 (4H, s), 7.1–7.9 (8H).

In a corresponding manner the following alkoxy methyl derivatives were prepared:

5-chloro-3-[1-[2-(3-dimethylaminomethyl-2-imidazolidinon-1-yl)ethyl]-4-piperidyl]-1-(4-fluorophenyl)-1H-indole, dioxalate hydrate, 6b. Mp: 145°–153° C. (decomp.). $^1$H NMR: δ2.02 (2H, broad q), 2.18 (2H, broad d),2.62 (6H, s), 3.12 (3H, m), 3.27 (2H t), 3.50 (8H, m), 4.33 (2H, s), 7.1–7.9 (8H);

5-chloro-3-[1-[2-(3-dipropylaminomethyl-2-imidazolidinon-1-yl)ethyl]-4-piperidyl]-1-(4-fluorophenyl)-1H-indole, dioxalate hydrate, 6c;

5-chloro-3-[1-[2-(3-t-butylaminomethyl-2-imidazolidinon-1-yl)ethyl]-4-piperidyl]-1-(4-fluorophenyl)-1H-indole, dioxalate, hydrate, 6d;

Example 7 (Method f)

5-Chloro-3-[1-[2-(3-ethoxymethyl-2-imidazolidinon-1-yl)ethyl]-4-piperidyl]-1-(4-fluorophenyl)-1H-indole, oxalate, 7a A solution of 5-chloro-1-(4-fluorophenyl)-3-[1 -[2-(2-imidazolidinon-1-yl)ethyl]-4-piperidyl]-1H-indole (4.4 g) and trifluoroacetic acid (5 ml) in ethanol (40 ml) was heated to 40° C. and 30% aqueous formaldehyde (800 mg) was added dropwise.

The mixture was heated for additionally 3 h at 40°–50° C. Most of the solvents was evaporated in vacuo and ice (200 g) and ethyl acetate were added. The pH was adjusted to >9 by addition of dil. NH$_4$OH. The organic phase was worked-up as above. The title compound crystallized as the oxalate salt from acetone. Yield: 3.1 g. Mp: 106°–107° C. (decomp.). $^1$H NMR: δ1.09 (3H, t), 1.98 (2H, broad q), 2.08 (2H, broad d), 3.05 (3H, m), 3.17 (2H, t), 3.40 (2H, q), 3.42 (4H, s), 3.48 (4H, m), 4.58 (2H, s), 7.1–7.9 (8H).

In a corresponding manner the following alkoxymethyl derivatives were prepared:

5-chloro-1-(4-fluorophenyl)-3-[1-[2-(3-methoxymethyl-2-imidazolidinon-1-yl)ethyl]-4-piperidyl]-1H-indole, oxalate, 7b. Mp: 100°–105° C. $^1$H NMR: δ2.00 (2H, broad q), 2.16 (2H, broad d), 3.03 (3H, m), 3.18 (3H, s), 3.20 (2H, t), 3.44 (4H, s), 3.52 (4H, m), 4.53 (2H, s), 7.1–7.9 (8H);

5-chloro-1-(4-fluorophenyl)-3-[1-[2-[3-(2-propyl)oxymethyl-2-imidazolidinon-1-yl]ethyl]-4-piperidyl]-1H-indole, oxalate, 7c. Mp: 96°–100° C. $^1$H NMR: δ1.10 (6H, d), 2.00 (2H, broad q), 2.17 (2H, broad d), 3.08 (3H, m), 3.21 (2h, t), 3.42 (4H, s), 3.49) (2H, t), 3.55 (2H, broad d), 3.60, (1H, h), 4.59 (2H, s), 7.1–7.9 (8H);

5-chloro-3-[1-[2-[3-(1-decanyl)oxymethyl-2-imidazolidinon-1-yl]ethyl]-4-piperidyl]-1-4-fluorophenyl)-1H-indole, 7d. Isolated as an oil. $^1$H NMR in chloroform-d: δ0.88 (3H, s), 1.27 (14H, broad s), 1.53 (2H, qui), 1.77 (2H, dq), 2.03 (2H, broad d), 2.20 (2H, dt), 2.58 (2H, t), 2.78 (1 H, tt) 3.07 (2H, broad d), 3.40 (2H, q), 3.42 (2H, t), 3.48 (4H, s), 4.69 (2H, s), 7.0–7.7 (8H).

Example 8 (Method a)

5-Chloro-1-(4-fluorophenyl)-3-[1-[2-[3-(4-isopropylbenzoyl)-2-imidazolidinon-1-yl]ethyl]-4-piperidyl]-1H-indole, fumarate, 8a To a cold solution of 5-chloro-1-(4-fluorophenyl)-3-[1-[2-(2-imidazolidinon-1-yl)ethyl]-4-piperidyl]-1H- indole (10.0 g)in dry toluene (100 ml) was added potassium carbonate (4.0 g). 4-Isopropylbenzoyl chloride (4.77 g) was added while keeping the temperature below 10° C. The mixture was stirred overnight and was then heated to 100° C. for 4 hours. Then the mixture was cooled, filtered and evaporated in vacuo. The residue was purified by chromatography on silica gel (eluted with ethyl acetate/triethylamine 95:5). Yield 5.53 g. The fumaric acid salt crystallized from ethanol: MP 196°–198° C. $^1$H NMR: $\delta$1.21 (6H, d), 1.77 (2H, dq), 2.05 (2H, broad d), 2.17 (2H, t), 2.56 (2H, t), 2.80 (1H, tt), 2.88 (1H, h), 3.04 (2H, broa 3.42 (2H, t), 3.58 (2H, t), 3.95 (2H, t), 7.0–7.7 (12H).

In a corresponding manner the following carboxylic acid derivatives were prepared:

5-chloro-3-[1-[2-[3-(2-chlorobenzoyl)-2-imidazolidinon-1-yl]ethyl]-4-piperidyl]-1-(4-fluorophenyl)-1H-indole, fumarate, 8b, MP: 209°–211° C. $^1$H NMR: $\delta$1.74 (2H, dq), 2.02 (2H, broad d), 2.16 (2H, dt), 2.58 (2H, t), 2.79 (1 H, tt), 3.00 (2H, broad d), 3.39 (2H, t), 3.66 (2H, t), 4.06 (2H, t), 7.0–7.7 (12H);

3-[1-[2-[3-(2-acetyloxybenzoyl )-2-imidazolidinon-1-yl]ethyl]-4-piperidyl]5-chloro-1-)4-fluorophenyl)-1H-indole, maleate, 8c, MP: 175°–177° C. $^1$H NMR: $\delta$1.75 (2H, dq), 2.07 (2H, broad d), 2.18 (2H, dt), 2.25 (3H, s), 2.57 (2H, t), 2.80 (1 H, tt), 3.03 (2H, broad d), 3.90 (2H, t), 3.61 (2H, t), 4.00 (2H, t), 7.0–8.2 (12H);

3-[1-[2-(3-butanoyl-2-imidazolidinon-1-yl)ethyl]-4-piperidyl]-5-chloro-1(4-fluorophenyl)-1H-indole, fumarate, 8d, MP: 181°–183° C. $^1$H $\delta$0.97 (3H, t), 1.69 (2H, sx), 1.78 (2H, dq), 2.07 (2H, broad d), 2.21 (2H, dt), 2.60 (2H, t), 2.82 (1H, tt), 2.92 (2H, t), 3.09 (2H, broad d), 3.44 ( 2H, t), 3.53 (2H, t), 3.85 (2H, t), 7.0–7.7 (8H).

5-chloro-1-(4-fluorophenyl)-3-[1-[2-(3-hexanoyl-2-imidazolidinon-1-yl)ethyl]-4-piperidyl]-1H-indole, fumarate, 8e, MP:110°–112° C. $^1$H NMR: $\delta$0.88 (3H, t), 1.30 (4H, m), 1.64 (2H, qui), 1.81 (2H, dq), 2.06 (2H, broad d), 2.22 (2H, dt), 2.62 (2H, t), 2.82 (1H, tt), 2.94 (2H, t), 3.13 (2H, broad d), 3.46 ( 2H, t), 3.52 (2H, t 7.0–7.7 (8H);

5-chloro-1-(4-fluorophenyl)-3-[1-[2-(3-octanoyl-2-imidazolidinon-1-yl)ethyl]-4-piperidyl]-1H-indole, fumarate, 8f, MP: 155°–157° C. $^1$H NMR: $\delta$0.88 (3H, t), 1.32 (6H, m), 1.66 (2H, qui), 1.82 (2H,d q), 2.06 (2H, broad d), 2.23 (2H, dt), 2.63 (2H, t), 2.81 (1 H, tt), 2.93 (2H, t), 3.11 (2H, broad d), 3.45 (2H, t), 3.50 (2H, t), 3.85 (2H, t), 7.0–7.7 (8H).

PHARMACOLOGY

Sertindole is a very potent Serotonin $S_2$ (5-HT$_2$) antagonist both in vitro and in vivo. The prodrugs of the invention were tested in vitro for 5-HT$_2$ receptor affinity ($^3$H-ketanserin binding) and for 5-HT$_2$ antagonistic effect in vivo (antagonism of quipazine induced head twiches). The tests which were well recognized and reliable tests, are described in the following and the results are shown in Table 1.

Inhibition of $^3$H-ketanserin Binding to Serotonin $S_2$ (5-HT$_2$) Receptors in Rat Cortex in vitro By this method the inhibition by drugs of the binding of $^3$H-Ketanserin (0,5 nM) to serotonin $S_2$ (5-HT$_2$) receptors in membranes from rat corex is determined in vitro. Method in Hyttel, *Pharmacol. & Toxicol*, 61, 126–129 1987.

Procedure

Male Wistar (Mol:Wist) rats are sacrificed and cortical tissue is dissected and weighed. The tissue is homogenized (Ultra Turrax, 10 sec.) in 10 ml of ice-cold 50 mM tris buffer pH 7.7 (at 25° C.). The centrifuge glass ware used in this step has been rinsed by sonication for 10 min. in ethanol. The homogenate is centrifuged twice at 20,000 g for 10 min. at 4° C. with rehomogenization of the pellet in 10 ml ice-cold buffer. The final pellet is homogenized in 500 vol (w/v) ice-cold buffer. Incubation tubes kept on ice in triplicate receive 100 $\mu$l of drug solution in water (or water for total binding) and 2000 $\mu$l of tissue suspension (final tissue content corresponds to 4 mg original tissue). The binding experiment is initiated by addition of 100 $\mu$l of $^3$H-Ketanserin (final concentration 0.5 nM) and by placing the tubes in a 37° C. water bath. After incubation for 30 min. the samples are filtered under vacuum (0–50 mBar) through Whatman GF/F filters (25 mm). The tubes are rinsed with 5 ml ice-cold buffer which are then poured on the filters. Thereafter, the filters are washed with 2×5 ml of buffer. The filters are placed in counting vials and 4 ml of appropriate scintillation fluid (e.g. Picofluor TM 15) are added. After shaking for 1 h and storage 2 hrs in the dark the content of radioactivity is determined by liquid scintillation counting. Specific binding is obtained by subtracting the nonspecific binding in the presence of 1 $\mu$M mianserin. For determination of the inhibition of binding five concentrations of drugs covering 3 decades are used.

The measured cpm are plotted against drug concentration on semilogarithmic paper and the best fitting S-shaped curve is drawn. The IC$_{50}$ value is determined as the concentration at which the binding is 50% of the total binding in control samples minus the nonspecific binding in the presence of 1 $\mu$M mianserin.

$^3$H-Ketanserin=[ethylene-$^3$H]-ketanserin hydrochloride from New England Nuclear, specific activity 60–80 Ci/mmol.

Quipazine Inhibition

Quipazine is a 5-HT$_2$ agonist, which induces head twitches in rats. The test is a test for 5-HT$_2$-antagonistic effect measuring the ability to inhibit head twitches. The method and test results for some reference substances are published by Arnt et al. (*Drug Dev. Res.*, 16, 59–70, 1989).

Procedure

Test substance is given p.o. 24 hrs before quipazine administration (6.8 mg/kg, s.c., dimaleate). Four rats, male Wistar (Mol:Wist) SPF rats, are used at each dose level. A control group is included each test day. After quipazine administration the rats are individually placed in the observation cages and head twitches are counted in an observation period of 10 min. 30–40 min. after injection of quipazine.

Total number of head twitches in each group are calculated and the result for each dose is expressed as percent of the response in the control group. ED$_{50}$ values are calculated by log-probit analysis. The test must be repeated if the average number of head twitches is lower than 9 in the control group.

TABLE 1

| Compound no. | $^3$H ketanserin binding IC$_{50}$ (nMol) | Quipazine inhibition (24 h, po) ED$_{50}$ ($\mu$mol/kg) |
|---|---|---|
| 1a | 1.2 | 0.029 |
| 1b | 57 | 0.09 |
| 1e | 47 | 0.77 |
| 1f | 9.3 | 0.05 |
| 2a | 260 | 0.55 |
| 4a | 0.90 | 0.24 |

TABLE 1-continued

| Compound no. | $^3$H ketanserin binding IC$_{50}$ (nMol) | Quipazine inhibition (24 h, po) ED$_{50}$ (μmol/kg) |
|---|---|---|
| 4d | 13 | 1.1 |
| 5a | 0.47 | 0.037 |
| 6a | 0.97 | 0.079 |
| 6b | 0.60 | |
| 7a | 1.2 | 0.081 |
| 7d | 49 | 0.15 |
| 8a | 20 | 0.12 |
| 8c | 24 | 0.057 |
| 8d | 5.6 | 0.014 |
| 8e | 38 | 0.039 |
| 8f | 140 | 0.092 |
| sertindole | 0.72 | 0.04 | it appears from Table 1 that some of the compounds of the invention have low in vitro 5-HT$_2$ activity, cf. the $^3$H ketanserin binding test, whereas they have high 5-HT$_2$ activity in vivo, cf. Quipazine inhibition test, indicating that they decompose to an active substance in vivo. Other compounds however have high activity both in vitro and in vivo. In this case the in vivo activity can be due to activity of the compound per se, mixed acitivity of the compound and sertindole or activity of sertindole.

Pharmacokinetics

The depot effects of the compounds of the invention were determined as described in the following example:

Animals and dosage

Seven Beagle dogs were used. One male and one female dog were used for each preparation exept for 1a where only one female dog was used. The compounds were dissolved in Viscoleo ®. One ml Viscoleo ® equivalent 1 kg dog. The dogs were dosed i.m. approx. 5 ml in each thigh.

Samples

Blood samples were drawn at 1,2, 4, 8, and 24 hours after dosing, and 2, 4, 7, 10, and 14 days after dosing.

Sertindole concentration in dog serum

The serum samples were analyzed by HPLC using a system consisting of a Spherisorb S5W column (25 cm × 4.6 mm) and a Hewlett Packard HP 1090 chromatograph with a HP 1050 UV-absorbance detector with a measuring wavelength of 254 nm. Elution was performed with n-heptane/2-propanol/conc. ammonia/water in the ratio 100/18.4/0.5/0.2, v/v as eluent at ambient temperature with a pressure of approximately 70 bar and a flow rate of 1 ml/min. The results are shown in FIGS. 1 and 2.

Results

Figure 1:
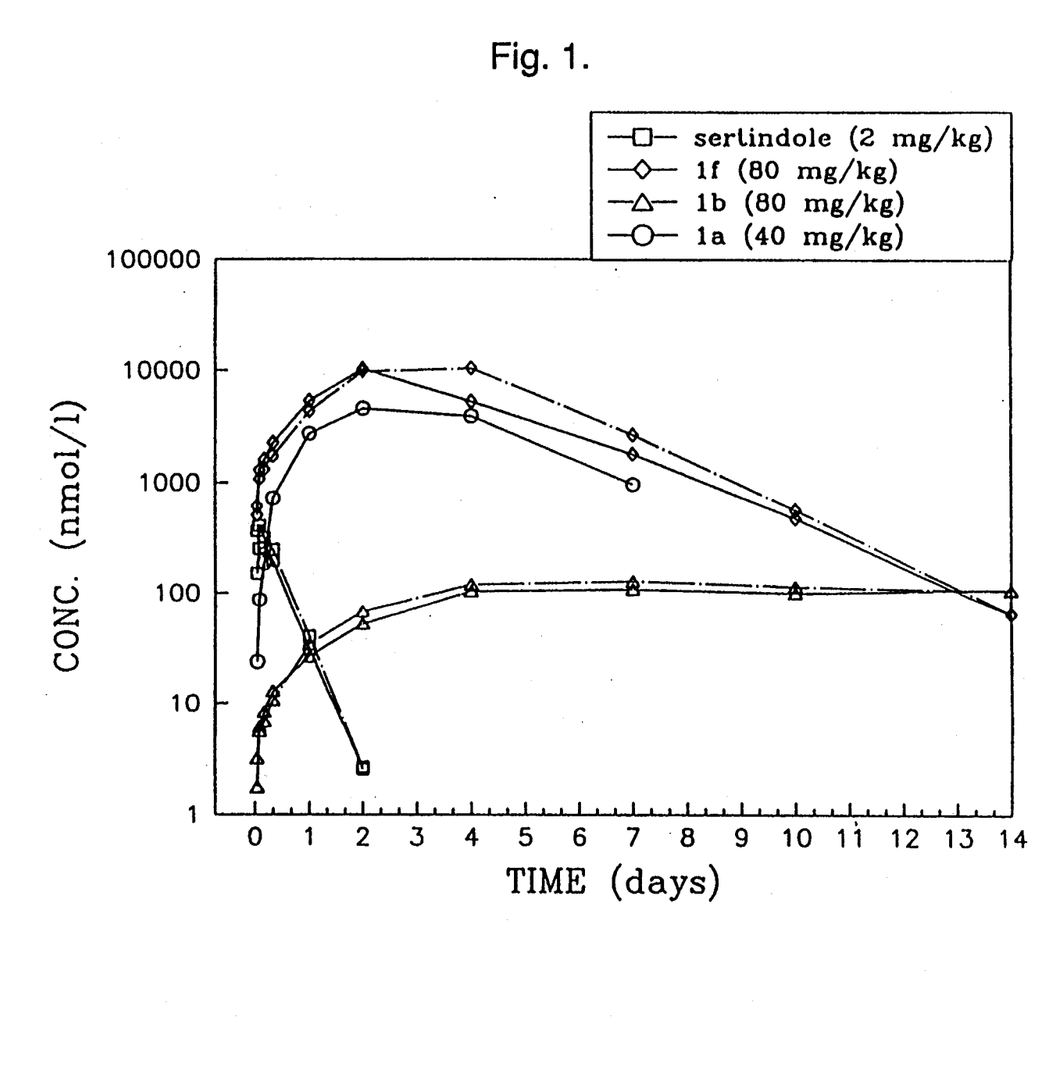
FIG. 1 shows the concentration of sertindole in dog serum samples, measured by HPLC versus time after administration of sertindole and compounds 1a, 1b and 1f of the invention.
Figure 2:
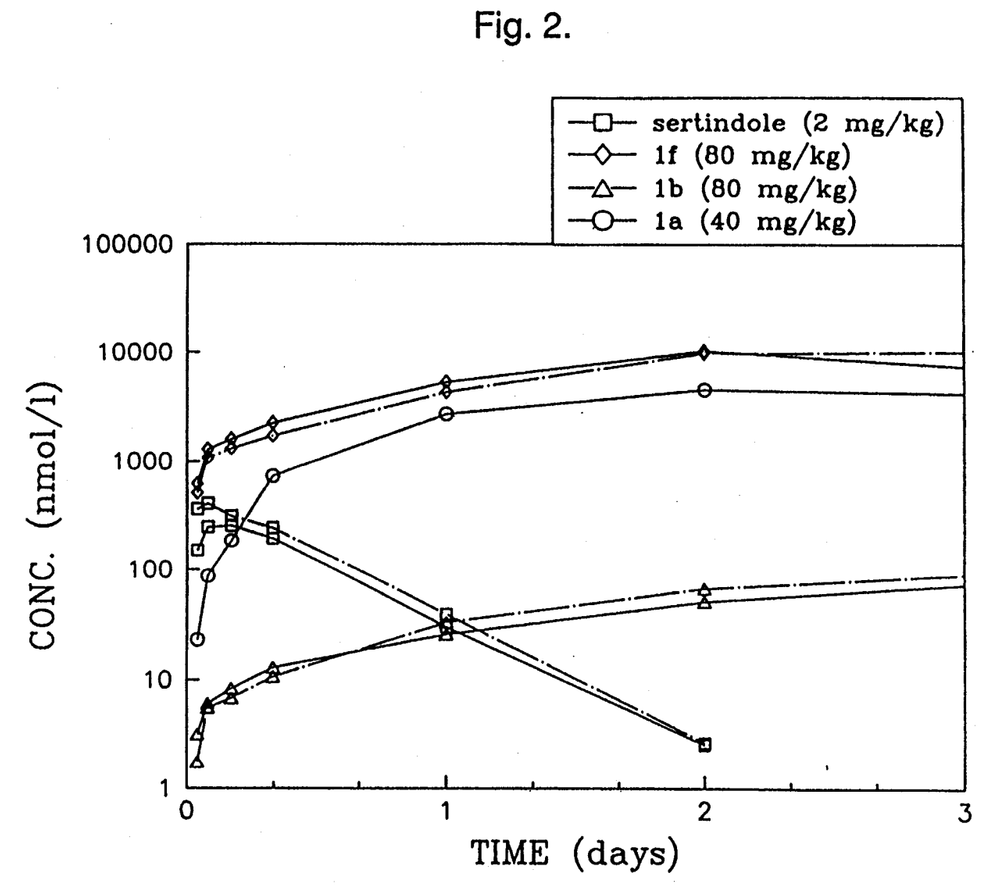
FIG. 2 is the initial section of FIG. 1 with expanded time axis showing the concentration of sertindole in dog serum samples versus time within the first 3 days after administration of test preparation.

FIGS. 1 and 2 show the sertindole concentration with time in the blood after application of sertindole and compounds of the invention, respectively. It is seen that application of a compound of the invention results in a prolonged release of sertindole to the serum. As shown in FIG. 1 also compounds which were found to have high in vitro activity, as e.g. compound 1a, decompose to sertindole after injection of a depot formulation.

Accordingly it is seen that the compounds of the present invention are sertindole prodrugs useful as depot preparation for prolonged release of sertindole to the body.

Formulation Examples

| Example A | |
|---|---|
| Compound 1a | 20 mg |

-continued

| | |
|---|---|
| Viscoleo ® | Ad 1.0 ml |
| Example B | |
| Compound 1b | 50 mg |
| Sesame oil BP | Ad 2.0 ml |
| Example C | |
| Compound 2a | 300 mg |
| Viscoleo ® | Ad 5.0 ml |
| Example D | |
| Compound 7d | 50 mg |
| Viscoleo ® | Ad 5.0 ml |

The solutions according to Examples A-D are made under sterile conditions by dissolving the compound of the invention in a part of the oil, adjusting to the desired volume and filling into suitable ampoules or vials.

We claim:

1. A sertindole prodrug having formula (1):

wherein X is selected from CO, CS, or CH$_2$, and if X is CO or CS, R is selected from the groups consisting of:
 i) hydrogen, C$_1$–C$_{24}$ alkyl, C$_2$–C$_{24}$ alkenyl, C$_3$–C$_8$ cycloalkyl, C$_3$–C$_8$ cycloalkenyl or C$_4$–C$_{32}$ cycloalk(en)ylalk(en)yl, optionally substituted with one or two hydroxy groups, or phenyl optionally substituted with one or more substituents selected from the group consisting of halogen, trifluoromethyl, C$_1$–C$_4$ alkyl, C$_1$–C$_4$ alkoxy, C$_1$–C$_4$ alkylthio, acyloxy, or cyano; or
 ii) YR$^1$, wherein Y is O or S and R$^1$ is selected from the substituents defined for R under i) above; and
 iii) NR$^2$R$^3$, wherein R$^2$ and R$^3$ independently are selected from the substituents defined for R under i) above or R$^2$ and R$^3$ are combined to form a four to eight member heterocyclic ring containing from one to three nitrogen atoms and from zero to three oxygen or sulfur atoms; or
if X is CH$_2$, R is selected from the groups consisting of:
 iv) a group YR$^1$ as defined in ii);
 v) a group NR$^2$R$^3$ as defined in iii); or
 vi) a group OC(O)R$^4$, wherein R$^4$ is as defined for R$^1$;
and pharmaceutically acceptable salts thereof.

2. The sertindole prodrug according to claim 1, wherein
 a) X is CO and R is C$_1$–C$_{10}$-alkyl or optionally substituted phenyl; or
 b) X is CH$_2$ and R is a group NR$^2$R$^3$, R$^2$ being hydrogen or C$_1$–C$_{10}$-alkyl and R$^3$ being C$_1$–C$_{10}$-alkyl, a 1-morpholino group, a group OCOR$^4$, R$^4$ being C$_1$–C$_{10}$-alkyl or a group YR$^1$ wherein Y is O and R$^1$ is C$_1$–C$_{10}$-alkyl.

3. The sertindole prodrug according to claim 2, selected from the group consisting of:
 3-[1-[2-(3-acetyl-2-imidazolidinon-1-yl)ethyl)-4-piperidyl]-5-chloro-1-(4-fluorophenyl)-1H-indole, 5-chloro-3-[1-[2-(3-decanoyl-2-Imidazolidinon-1-yl)ethyl]-4-piperidyl]-1-(4-fluorophenyl)-1H-indole, 3-[1-[2-(3-benzoyl-2-Imidazolidinon-1-yl)ethyl]-4-piperidyl]-5-chloro-1-(4-fluorophenyl)-1H-indole, 5-chloro-1-(4-fluorophenyl)-3-[1-[2-[3-(1-morpholinomethyl)-2-imidazolidinon-1-yl]ethyl]-4-piperidyl]-1H-indole, 5-chloro-1-(4-fluorophenyl)-3-[1-[2-(3-butanoyl-2-imidazolidinon-1-yl)ethyl]-4-1H-indole, 5-chloro-3-[1-[2-[3-(1-decanyl)oxymethyl-2-imidazolidinon-1-yl]ethyl]-4-piperidyl]-1-(4-fluorophenyl)-1H-indole, 5-chloro-1-(4-fluorophenyl)-3-[1-[2-(3-hexanoyl-2-imidazolidinon-1-yl)ethyl]-4-piperidyl]-1H-indole, and 5-chloro-1-(4-fluorophenyl)-3-[1-[2-(3-octanoyl-2-imidazolidinon-1-yl)ethyl]-4-piperidyl]-1H-indole.

4. A pharmaceutical composition, comprising a therapeutically effective amount of a sertindole prodrug according to claim 1 and a pharmaceutically acceptable carrier or diluent.

5. The pharmaceutical composition according to claim 4, comprising a therapeutically effective amount of a prodrug derivative according to claim 1 or a pharmacologically acceptable acid addition salt thereof in a suitable pharmaceutical formulation.

6. A depot composition for injection intra muscularis comprising a therapeutically effective amount of a prodrug according to claim 1 or a pharmacologically acceptable acid addition salt thereof in a suitable pharmaceutically acceptable oil.

7. The depot formulation according to claim 6, wherein the pharmaceutically acceptable oil is selected from the group consisting of coconut oil, peanut oil, sesame oil, cotton seed oil, corn oil, soy bean oil, olive oil, and esters, of fatty acids and polyfunctional alcohols.

8. A method for the treatment of schizophrenia comprising administering to a mammal in need of such treatment a prodrug according to claim 1 or a pharmaceutically acceptable acid addition salt thereof.

9. A method for the treatment of non-schizophrenic psychoses comprising administering to a mammal in need of such treatment a prodrug according to claim 1 or a pharmaceutically acceptable acid addition salt thereof.

10. A method for the treatment of depression comprising administering to a mammal in need of such treatment a prodrug according to claim 1 or a pharmaceutically acceptable acid addition salt thereof.

11. A method for the treatment of anxiety comprising administering to a mammal in need of such treatment a prodrug according to claim 1 or a pharmaceutically acceptable acid addition salt thereof.

* * * * *

UNITED STATES PATENT AND TRADEMARK OFFICE
CERTIFICATE OF CORRECTION

PATENT NO. : 5,428,036
DATED : June 27, 1995
INVENTOR(S) : Jens Kristian PERREGAARD and Henrik PEDERSON It is certified that errors appear in the above-identified patent and that said Letters Patent is hereby corrected as shown below:

Column 14, line 61, please delete "," and replace with - - ; or $NR^2R^3$ is - -

Column 14, line 62, after "1-morpholino group", delete "," and replace with - -; or R is - -

Signed and Sealed this

Twenty-seventh Day of June, 2000

Attest:

Q. TODD DICKINSON

*Attesting Officer*     *Director of Patents and Trademarks*